United States Patent
Okada et al.

(10) Patent No.: US 10,292,913 B2
(45) Date of Patent: May 21, 2019

(54) POWDERED TOBERMORITE-TYPE CALCIUM SILICATE-BASED MATERIAL AND METHOD FOR PRODUCING SAME

(71) Applicant: TOMITA PHARMACEUTICAL CO., LTD., Naruto-shi, Tokushima (JP)

(72) Inventors: Yuka Okada, Naruto (JP); Kazuki Kamai, Naruto (JP); Yuuta Tsumura, Naruto (JP); Yukinori Konishi, Naruto (JP)

(73) Assignee: TOMITA PHARMACEUTICAL CO., LTD., Naruto-shi (JP)

( * ) Notice: Subject to any disclaimer, the term of this patent is extended or adjusted under 35 U.S.C. 154(b) by 0 days.

(21) Appl. No.: 15/128,868

(22) PCT Filed: Mar. 26, 2015

(86) PCT No.: PCT/JP2015/059382
§ 371 (c)(1),
(2) Date: Sep. 23, 2016

(87) PCT Pub. No.: WO2015/151997
PCT Pub. Date: Oct. 8, 2015

(65) Prior Publication Data
US 2017/0112735 A1 Apr. 27, 2017

(30) Foreign Application Priority Data

Mar. 29, 2014 (JP) .................. 2014-070672

(51) Int. Cl.
| | |
|---|---|
| *B01J 20/10* | (2006.01) |
| *A61K 8/25* | (2006.01) |
| *A61Q 19/02* | (2006.01) |
| *C01B 33/24* | (2006.01) |
| *B01J 20/28* | (2006.01) |
| *A61K 8/02* | (2006.01) |

(52) U.S. Cl.
CPC .............. *A61K 8/25* (2013.01); *A61K 8/0279* (2013.01); *A61Q 19/02* (2013.01); *B01J 20/10* (2013.01); *B01J 20/28004* (2013.01); *B01J 20/28057* (2013.01); *B01J 20/28061* (2013.01); *B01J 20/28073* (2013.01); *B01J 20/28083* (2013.01); *B01J 20/28085* (2013.01); *B01J 20/28092* (2013.01); *C01B 33/24* (2013.01); *A61K 2800/60* (2013.01); *A61K 2800/80* (2013.01); *C01P 2006/14* (2013.01); *C01P 2006/16* (2013.01)

(58) Field of Classification Search
CPC ......... A61K 8/25; A61K 8/0279; B01J 20/10; B01J 20/28004
See application file for complete search history.

(56) References Cited

FOREIGN PATENT DOCUMENTS

| JP | 2005-179148 A | 7/2005 |
| JP | 2007-238412 A | 9/2007 |
| WO | WO-2002/066396 A1 | 8/2002 |

OTHER PUBLICATIONS

Yamamoto, T. et al, Influence of KOH on the Hydrothermal Reaction between Siliceous Waste Material and $CaCO_3$, Solvothermal Reactions, vol. 2, Feb. 25, 1997, pp. 110-113.
Gabrovsek, R. et al, Tobermorite formation in the system CaO, $C_3S$-$SiO_2$-$Al_2O_3$-NaOH-$H_2O$ under hydrothermal conditions, Cement and Concrete Research, 1993, vol. 23, pp. 321-328.

*Primary Examiner* — Gina C Justice
(74) *Attorney, Agent, or Firm* — Locke Lord LLP

(57) ABSTRACT

Provided is a powdered tobermorite-type calcium silicate-based material capable of demonstrating high oil absorption. The powdered tobermorite-type calcium silicate-based material is characterized in that (1) a molar ratio of $SiO_2$/CaO in the material is 1.5 or more, and (2) a cumulative pore volume having a pore size of 3.6 nm to 200 nm in the material is 0.9 cc/g or more, and a cumulative pore volume having a pore size of 3.6 nm to 5000 nm is 2.6 cc/g or more.

8 Claims, 3 Drawing Sheets

(a)　　　　　　　(b)　　　　　　　(c)

(a)　　　　　　　(b)　　　　　　　(c)

10,292,913 B2

POWDERED TOBERMORITE-TYPE CALCIUM SILICATE-BASED MATERIAL AND METHOD FOR PRODUCING SAME

BACKGROUND OF THE INVENTION

1. Field of the Invention

The present invention relates to a novel powdered tobermorite-type calcium silicate-based material and to a method for producing the same.

2. Description of the Related Art

Calcium silicate is a compound that has a long history and consists of both natural and synthetic forms. In addition, known crystal forms of calcium silicate include gyrolite, wollastonite and tobermorite. Calcium silicate is used in various applications, including building materials (such as lagging materials, refractory materials or heat insulating materials), as well as pharmaceutical additives, food additives, fillers, thickeners, matting agents and carriers.

Among these various types of calcium silicate, calcium silicate having high oil absorption in particular is used in pharmaceutical additives such as excipients, carriers, binders or disintegrating agents, as carriers of liquid substances in cosmetic and industrial fields, and as carriers of perfumes or oxygen adsorbing agents. Since tobermorite-type calcium silicate in particular has a higher specific surface area than other crystal forms and is superior for use as a carrier, research is proceeding on the development of porous materials of tobermorite-type calcium silicate.

A known example of a method used to produce calcium silicate consists of producing calcium silicate (tobermorite crystals) from a silicic acid raw material and a calcareous raw material by a hydrothermal synthesis reaction (for example, Japanese Patent Application Publication No. H06-329409 or Japanese Patent Application Publication No. H06-40715).

On the other hand, as a method that does not use a hydrothermal reaction, a method for producing porous calcium silicate has been proposed, which includes: a slurry formation step of blending a silicic acid raw material and a lime raw material within a range of the molar ratio of $CaO/SiO_2$ of 0.4 to 1.0 followed by adding water and suspending to form a slurry; a mechanochemical reaction step of simultaneously agitating and crushing the formed slurry using a wet grinder to produce a mechanochemical reaction; and a heat curing step of heat-curing the slurry following the mechanochemical reaction while agitating (Japanese Patent Application Publication No. 2004-43290).

SUMMARY OF THE INVENTION

However, the calcium silicate obtained by a hydrothermal synthesis reaction such as that of Japanese Patent Application Publication No. H06-329409 or H06-40715 still has room for improvement with respect to oil absorption and the like. Moreover, a large amount of energy is consumed in the hydrothermal synthesis reaction, making it disadvantageous in terms of cost in the case of production on an industrial scale. In addition, in the production method using a mechanochemical reaction in the manner of Japanese Patent Application Publication No. 2004-43290, contamination by impurities attributable to wet grinding (or the media) cannot be avoided. Consequently, this method is not suitable for applications such as pharmaceuticals requiring a high level of purity.

Thus, a primary object of the present invention is to provide a powdered tobermorite-type calcium silicate-based material having high oil absorption.

As a result of conducting extensive research in consideration of the problems of the related art, the inventor of the present invention found that a tobermorite-type calcium silicate-based material incorporating silicon dioxide (hydrated silicon dioxide) produced according to a specific method within the structure thereof is able to realize superior liquid absorbing properties as a result of having a specific pore structure, thereby leading to completion of the present invention.

The present invention is directed to a tobermorite-type calcium silicate-based material and a method for producing the same as indicated below.

1. A powdered tobermorite-type calcium silicate-based material, wherein
(1) a molar ratio of $SiO_2/CaO$ in the material is 1.5 or more, and
(2) a cumulative pore volume having a pore size of 3.6 nm to 200 nm in the material is 0.9 cc/g or more, and a cumulative pore volume having a pore size of 3.6 nm to 5000 nm is 2.6 cc/g or more.

2. The powdered tobermorite-type calcium silicate-based material described in 1 above, wherein an integrated intensity ratio during powder X-ray diffraction analysis [(integrated intensity when peak location represented by $2\theta/\theta=32.00°$)/(integrated intensity when peak location represented by $2\theta/\theta=25.00°$)] is 0.01 to 0.20.

3. The powdered tobermorite-type calcium silicate-based material described in 1 above, wherein a BET specific surface area is 100 $m^2/g$ to 500 $m^2/g$.

4. The powdered tobermorite-type calcium silicate-based material described in 1 above, wherein an average particle diameter is 1 µm to 100 µm.

5. A method for producing the powdered tobermorite-type calcium silicate-based material described in any of 1 to 4 above,
the method including:
(1) a first step of obtaining a first aqueous slurry containing a first reaction product by adding an alkali to a calcium-containing liquid, which is obtained by dispersing or dissolving a calcium raw material in an aqueous medium, and allowing to react;
(2) a second step of obtaining a second aqueous slurry containing a second reaction product by adding a silicic acid raw material to the first aqueous slurry, or an aqueous slurry for which a water content thereof has been adjusted, and allowing to react; and
(3) a third step of obtaining a third aqueous slurry containing a tobermorite-type calcium silicate-based material by adjusting pH of the second aqueous slurry or aqueous slurry obtained by adjusting a water content thereof.

6. The production method described in 5 above, further comprising a step of aging the second reaction product for a fixed period of time at 70° C. or lower, prior to the third step.

7. A powdered tobermorite-type calcium silicate-based material, which is obtained according to the production method described in 5 above.

8. A deoxidizing agent, having a readily oxidizable component loaded on the powdered tobermorite-type calcium silicate-based material described in any of 1 to 4 above.

9. A cosmetic containing the powdered tobermorite-type calcium silicate-based material described in any of 1 to 4 above.

10. The cosmetic described in 9 above, having melanin loaded on the powdered tobermorite-type calcium silicate-based material.

11. A cosmetic for adsorbing or removing melanin containing the powdered tobermorite-type calcium silicate-based material described in any of 1 to 4 above.

The tobermorite-type calcium silicate-based material of the present invention is able to demonstrate superior liquid absorbing properties as a result of having a specific composition and pore structure.

In addition, the production method of the present invention allows a tobermorite-type calcium silicate-based material having a specific pore structure as described above to be reliably obtained. Moreover, the production method of the present invention differs from synthesis methods carried out under harsh conditions in the manner of mechanochemical methods or hydrothermal synthesis reaction methods in that synthesis can be carried out under comparatively mild conditions, thereby making it advantageous for production on an industrial scale. In addition, differing from mechanochemical methods, since there are hardly any opportunities for contamination by impurities, materials of comparatively high purity can be produced.

Although a calcium silicate-based material having properties as described above can be used in the same applications as those of known or commercially available calcium silicate, it is particularly effective as a pharmaceutical additive, food additive, cosmetic raw material or industrial raw material and the like based on the properties thereof. It is particularly preferable as an excipient, binder, disintegrating agent or carrier of a pharmaceutical or as a carrier of a deoxidizing agent. For example, it can be used in the form of a preparation containing the calcium silicate of the present invention and an active ingredient (such as a pharmaceutical, food, cosmetic or deoxidizing agent).

DESCRIPTION OF THE PREFERRED EMBODIMENTS

1. Powdered Tobermorite-Type Calcium Silicate-Based Material

Figure 1:
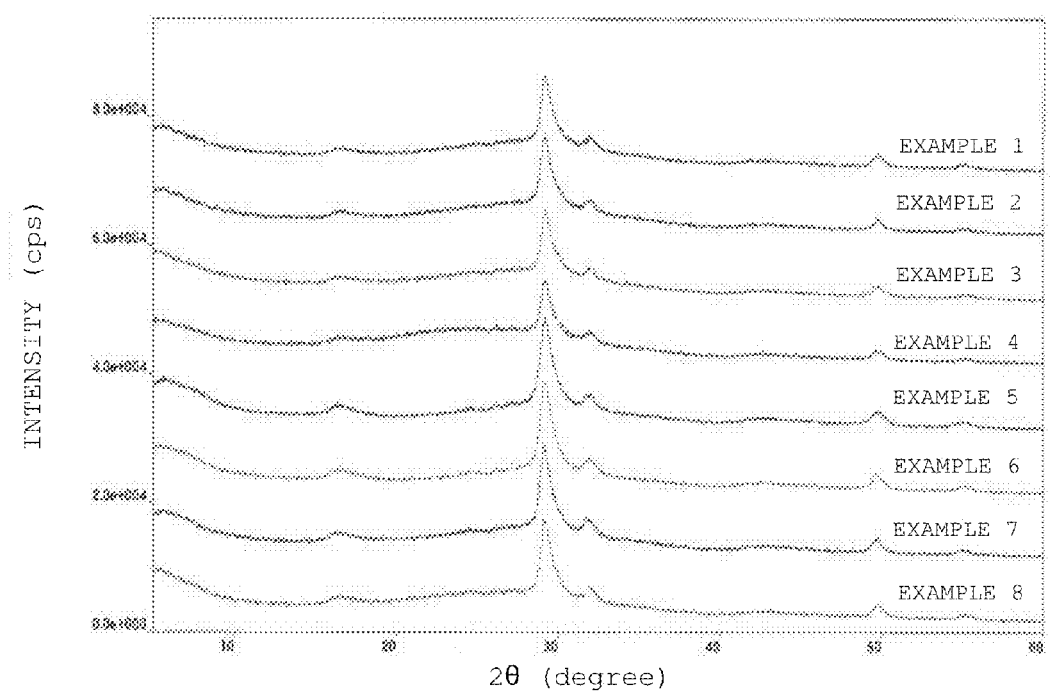
FIG. 1 is a graph showing the results of analyzing each of the samples of Examples 1 to 8 by powder X-ray diffraction analysis.

The tobermorite-type calcium silicate-based material of the present invention (material of the present invention) is a powdered tobermorite-type calcium silicate-based material characterized in that:

(1) the molar ratio of $SiO_2/CaO$ in the material is 1.5 or more, and (2) the cumulative pore volume having a pore size of 3.6 nm to 200 nm in the material is 0.9 cc/g or more, and the cumulative pore volume having a pore size of 3.6 nm to 5000 nm is 2.6 cc/g or more.

The material of the present invention contains as main components thereof silicon dioxide and calcium silicate having a tobermorite crystal structure. This calcium silicate-containing material is a tobermorite-type calcium silicate-based material represented by the compositional formula $5CaO \cdot 7SiO_2 \cdot nSiO_2 \cdot mH_2O$ (wherein, n and m satisfy the relationships of $0.5 \leq n$ and $0 \leq m$).

The molar ratio of $SiO_2/CaO$ in the material of the present invention is 1.5 or more, preferably 1.5 to 2.9 and more preferably 1.5 to 2.3. In the case the above-mentioned molar ratio of $SiO_2/CaO$ is less than 1.5, tobermorite-type calcium silicate incorporating silicon dioxide is not formed thereby the specific pore structure cannot be fully formed. Furthermore, although there are no particular limitations thereon, the upper limit value of the above-mentioned molar ratio is typically about 5.0. Namely, since the compositional ratio of tobermorite-type calcium silicate is such that the $SiO_2/CaO$ is 1.0 to 1.4, the material of the present invention has a composition in which the silica component (silicon component) is contained in a larger amount than the stoichiometric value of the $SiO_2/CaO$ molar ratio of tobermorite-type calcium silicate. Thus, the silica component (and particularly, amorphous silicon dioxide) and tobermorite-type calcium silicate crystals are inseparably contained in a single particle that composes the powder of the material of the present invention. This inseparable structure per se is derived from, for example, the composition/structure possessed by a calcium silicate-containing co-precipitate obtained by reacting a calcium raw material and a silicic acid raw material in the liquid phase. With respect to this point, this differs from a simple mixed powder of tobermorite-type calcium silicate powder and silicon dioxide powder. In addition, the structure thereof is such that tobermorite-type calcium silicate is in a state inseparably incorporating silicon dioxide, and as a result thereof, it differs from ordinary tobermorite crystals having a plate-like structure, and this is thought to enable the formation of a porous structure unique to the material of the present invention.

A peak corresponding to amorphous silicon dioxide is also preferably observed particularly in a powder X-ray diffraction (XRD) analysis of the material of the present invention, having a composition and structure as previously described, in addition to a peak corresponding to tobermorite-type calcium silicate. More specifically, a peak preferably appears at $2\theta=32.00$ (peak corresponding to tobermorite-type calcium silicate) and at $2\theta=25.00$ (peak containing a peak corresponding to amorphous silicon dioxide).

Furthermore, although a well-defined peak is not observed in an XRD analysis of the silicon dioxide present in the material of the present invention since it is amorphous, a broad peak having its apex at 2θ=25° is detected when amorphous silicon dioxide is present. Since the material of the present invention contains a silica component in an amount that is greater than the stoichiometric proportion (molar ratio of $SiO_2/CaO=1.4$), the peak in the vicinity of 2θ=25° characteristic of tobermorite-type calcium silicate crystal (refer to, for example, Comparative Example 2 of FIG. 2) cannot be confirmed to be a well-defined peak in the vicinity of 2θ=25° based on tobermorite-type calcium silicate crystals due to the broad peak derived from amorphous silicon dioxide. This is thought to represent a state in which tobermorite-type calcium silicate crystals inseparably incorporate silicon dioxide. Therefore, in the material of the present invention, the integrated intensity of the broad peak at 2θ=25.00° can be deliberately quantified by treating the broad peak in the vicinity of 2θ=25° as a complex peak of amorphous silicon dioxide and tobermorite-type calcium silicate crystals. In this manner, the material of the present invention is preferably a composite inseparably composed of tobermorite-type calcium silicate crystals and amorphous silicon dioxide (composite resembling a mixed crystal).

Although there are no particular limitations thereon, the integrated intensity ratio of both peaks in this case [(integrated intensity when peak location represented by 2θ/θ=) 32.00°/(integrated intensity when peak location represented by 2θ/θ=25.00°)] is particularly preferably 0.01 to 0.20. Higher porosity can be exhibited by having an integrated intensity ratio within this range.

The cumulative pore volume having a pore size of 3.6 nm to 200 nm in the material of the present invention is 0.9 cc/g or more and preferably 1.0 cc/g or more. In the case the above-mentioned cumulative pore volume is less than 0.9 cc/g, high oil absorption cannot be performed. Thus, high oil absorption can be obtained more reliably by setting such cumulative pore volume. Furthermore, although there are no particular limitations thereon, the upper limit value of the cumulative pore volume having a pore size of 3.6 nm to 200 nm is normally about 3.0 cc/g.

In addition, the cumulative pore volume having a pore size of 3.6 nm to 5000 nm in the material of the present invention is normally 2.6 cc/g or more, preferably 3.0 cc/g or more and more preferably 3.3 cc/g or more. High oil absorption can be obtained more reliably by setting cumulative pore volume in this manner. Furthermore, although there are no particular limitations thereon, the upper limit value of the cumulative pore volume having a pore size of 3.6 nm to 5000 nm is normally about 6.0 cc/g.

The material of the present invention preferably has high porosity. Thus, BET specific surface area is also normally about 50 m$^2$/g to 400 m$^2$/g, and particularly preferably 100 m$^2$/g to 400 m$^2$/g. The adoption of such a porous structure makes it possible to obtain higher liquid absorbing properties.

In addition, although not limiting, oil absorption of the material of the present invention is particularly 2.5 mL/g or more, and more preferably 2.7 mL/g or more. Namely, since the material of the present invention has a specific $SiO_2/CaO$ ratio and a specific pore volume, it allows the obtaining of high oil absorption attributable to the pore structure thereof.

The material of the present invention has the form of a powder. Although the average particle diameter thereof can be suitably set corresponding to, for example, the application or usage method of the material of the present invention, it is normally about 1 μm to 100 μm, particularly 1 μm to 50 μm, and more preferably 5 μm to 25 μm.

The material of the present invention can preferably use a powdered tobermorite-type calcium silicate-based material obtained according to the production method of the present invention indicated in, for example, "3. Method for Producing Material of Present Invention" to be subsequently described.

Although the material of the present invention can be used in the same applications as applications of known or commercially available calcium silicate, it is particularly effective as a pharmaceutical additive, food additive, cosmetic raw material or industrial raw material and the like based on the properties thereof. It is particularly preferable as an excipient, binder, disintegrating agent or carrier of a pharmaceutical or as a carrier of a deoxidizing agent. For example, the material of the present invention can be used in the form of a preparation containing the calcium silicate of the present invention and an active ingredient (such as a pharmaceutical, food, cosmetic or deoxidizing agent). Thus, there are no limitations on the form in which it is used, and may be used, for example, directly as a powder or may be granulated or shaped corresponding to the application and the like.

2. Deoxidizing Agent

The present invention includes a deoxidizing agent that contains the powdered tobermorite-type calcium silicate-based material according to the present invention (material of the present invention) and an easily oxidizable component.

In the present invention, an easily oxidizable organic compound can be used for the easily oxidizable component. Known compounds used in deoxidizing agents can be used for the easily oxidizable organic compound. For example, at least one type of ascorbic acid, ascorbates, erythorbic acid, erythorbates, ethylene glycol, propylene glycol, catechol, gallic acid, resorcin, hydroquinone, pyrogallol, tocopherol, glucose, xylose, xylitol, sorbitol, mannitol, glycerin, butadiene oligomers, isoprene oligomers, fish oil, tall oil or unsaturated fatty acids can be used.

There are no particular limitations on the content of the easily oxidizable organic compound, and may typically be suitably set within a range of 60 parts by weight to 400 parts by weight, preferably 60 parts by weight to 300 parts by weight, and more preferably 60 parts by weight to 120 parts by weight, based on 100 parts by weight of the powdered tobermorite-type calcium silicate-based material.

In addition, the deoxidizing agent of the present invention can also contain an additive (accelerator) that accelerates the deoxygenation reaction as necessary. Known compounds used in deoxidizing agents can be used for such additives. For example, at least one type of metal compound can be used. More specifically, at least one type of alkaline agent, such as an alkaline metal or alkaline earth metal hydroxide, carbonate or bicarbonate, or at least one type of transition metal salt catalyst, such as a manganese salt, iron salt, cobalt salt or copper salt, can be used.

Although there are no particular limitations on the content of the above-mentioned accelerator, it may typically be suitably set within the range of 25 parts by weight to 160 parts by weight, preferably 25 parts by weight to 120 parts by weight, and more preferably 25 parts by weight to 50 parts by weight, based on 100 parts by weight of the powdered tobermorite-type calcium silicate-based material.

Moreover, the deoxidizing agent of the present invention may also contain other components so as not to adversely affect the advantages of the present invention. Examples thereof include metal oxides, organic binders, activated charcoal, silica gel, zeolite and calcium silicate other than the material of the present invention. Components similar to known or commercially available components used in deoxidizing agents may be used for these components.

The deoxidizing agent of the present invention can be produced by a method comprising a step of stirring a raw material containing the material of the present invention and an easily oxidizable component (mixing step). In the mixing step, a raw material containing the material of the present invention and a solid or liquid easily oxidizable component are preferably mixed or supported (impregnated). More specifically, an easily oxidizable component is preferably at least fixed in pores present in the material of the present invention.

In the mixing step, in addition to being able to be used directly in the form of a powder, the material of the present invention can also be used in the form of granules prepared by granulating in advance. In addition, although the easily oxidizable component may be in the form of a solid or liquid, it is ultimately made to be such that both the material of the present invention and the easily oxidizable component mix together in the presence of a solvent so that the easily oxidizable component can be fixed on the material of the present invention. Examples of methods that can be used include: 1) a method comprising a step of adding a solvent (and particularly water or aqueous solvent) to granules obtained by using a dry method to agitate or granulate a mixed powder containing the material of the present invention in the form of a dry powder and the easily oxidizable component in the form of a powder, and 2) a method comprising a step of agitating or granulating the material of the present invention in the form of a dry powder and at least a solution (and particularly, an aqueous solution), in which the easily oxidizable component is dissolved, or at least a dispersion (and particular, an aqueous dispersion), in which the easily oxidizable component is dispersed.

After having carried out the mixing step, a drying step may be carried out as necessary. The deoxidizing agent of the present invention can be obtained in this manner.

The deoxidizing agent of the present invention may be used in the same manner as known or commercially available deoxidizing agents, and for example, the deoxidizing agent of the present invention may be filled into an air-permeable package or container, or may be charged or fixed in various types of products (and particularly, in the packages of products).

3. Cosmetic

The present invention includes a cosmetic (a cosmetic composition) containing the powdered tobermorite-type calcium silicate-based material according to the present invention (material of the present invention).

The material of the present invention can be used as a constituent component of a cosmetic, and particularly that of a solid or paste-like cosmetic applied to skin (such as foundation, lip cream, eye shadow or facial pack). By using the material of the present invention as a constituent component of a cosmetic, although functions (such as moisture absorption, oil absorption or concealment) attributable to conventional calcium silicate can be obtained, since various types of functional components can be effectively supported on the material of the present invention in particular, profitable effects attributable to those functional components can also be reliably obtained.

Furthermore, in the cosmetic according to the present invention, components, composition ratios and the like similar to known or commercially available cosmetics can be used for components other than the material of the present invention.

Although the content of the material of the present invention in the cosmetic can be suitably set corresponding to, for example, the purpose of adding the material of the present invention, it is normally about 1% by weight to 95% by weight and particularly preferably 1% by weight to 65% by weight. As a result, the advantages of the material of the present invention can be obtained more reliably.

In particular, the material of the present invention can be preferably used as a constituent component of a cosmetic having functions like that indicated in a) and b) below.

a) Ultraviolet Light Blocking Function

Since the material of the present invention can be loaded with a comparatively large amount of an ultraviolet light absorbing component, a cosmetic containing the material of the present invention is expected to have a high level of ultraviolet light blocking performance. Although there are no particular limitations on the ultraviolet light absorbing component, melanin can be used particularly preferably. Namely, as a result of containing a powder, in which melanin is supported on the material of the present invention, in a cosmetic, the ultraviolet light absorbing effect of the melanin can be obtained more efficiently.

There are no particular limitations on the content of the ultraviolet light absorbing component, and may be typically be suitably set within a range of 1 part by weight to 99 parts by weight, preferably 20 parts by weight to 99 parts by weight, and more preferably 25 parts by weight to 99 parts by weight, based on 100 parts by weight of the powdered tobermorite-type calcium silicate-based material.

The method for loading an ultraviolet light absorbing component such as melanin on the material of the present invention may be similar to a known method. For example, melanin can be supported by a method comprising a step of impregnating the material of the present invention with a solution obtained by dissolving an ultraviolet light absorbing component such as melanin in a solvent. That is, a powder can be obtained in which melanin is loaded in the material of the present invention. A drying step and the like may be carried out as necessary after impregnating the material of the present invention with melanin.

b) Melanin Pigment Adsorption and Removal Function

Since the material of the present invention can maintain melanin in the manner of a) as previously described, it can also be applied to adsorption and removal of melanin in skin.

For example, aluminum silicate is known to be a melanin adsorber used for the purpose of adsorbing and removing melanin (melanin pigment), and the material of the present invention can also be preferably used as a melanin adsorbent. Since the material of the present invention is insoluble in water and is composed of particles having a particle diameter of 1 μm to 100 μm in the same manner as ordinary melanin adsorbents, it has difficulty in penetrating the skin. Consequently, an effect that decreases melanin pigment can be expected to be performed as a result of promoting entry of the material of the present invention into skin tissue by incorporating a keratolytic agent (for example, urea and salicylate). Namely, by containing the material of the present invention in a cosmetic, a high level of melanin adsorption and removal performance can be obtained.

4. Method for Producing Material of Present Invention

The powdered tobermorite-type calcium silicate-based material of the present invention can be preferably produced according to the production method described below in particular. Namely, the method for producing the powdered tobermorite-type calcium silicate-based material of the present invention is comprised of:

(1) a first step of obtaining a first aqueous slurry containing a first reaction product by adding an alkali to a calcium-containing liquid, the liquid being obtained by dispersing or dissolving a calcium raw material in an aqueous medium, and allowing to react;

(2) a second step of obtaining a second aqueous slurry containing a second reaction product by adding a silicic acid raw material to the first aqueous slurry or an aqueous slurry prepared by adjusting the water content of the first aqueous slurry, and allowing to react; and, (3) a third step of obtaining a third aqueous slurry containing a tobermorite-type calcium silicate-based material by adjusting the pH of the second aqueous slurry or an aqueous slurry obtained by adjusting the water content of the second aqueous slurry.

First Step

In the first step, a first slurry containing a first reaction product is obtained by adding an alkali to a calcium-containing liquid obtained by dispersing or dissolving a calcium raw material in an aqueous medium, and allowing to react.

The calcium-containing liquid used in the first step is prepared by, for example, dispersing or dissolving a calcium raw material in an aqueous medium.

The above-mentioned calcium raw material is not limited, and a calcium supply source similar to that used in the production of known calcium silicate can be used. Examples of water-soluble calcium raw materials include calcium chloride, calcium nitrate and water-soluble calcium salt of organic acids. Examples of water-insoluble or poorly water-soluble calcium raw materials include calcium oxide, calcium hydroxide, calcium carbonate, calcium sulfate and insoluble calcium salt of organic acids. In the present invention, at least one type of calcium raw material such as calcium chloride, calcium nitrate, calcium hydroxide or calcium oxide can be used particularly preferably from the viewpoint that the reaction with the silicic acid raw material is carried out specifically due to the coexistence of calcium hydroxide and calcium ions in the reaction solution.

The calcium-containing liquid may be any of, for example, 1) a solution in which a calcium raw material is dissolved in an aqueous medium (namely, a solution containing calcium ions), 2) a dispersion in which a calcium raw material is dispersed in an aqueous medium, or 3) a mixture containing calcium ions and a calcium raw material dispersed in an aqueous medium.

At least one of water and water-soluble organic solvent can be used as the aqueous medium. Examples of water-soluble organic solvents that can be used include alcohols, such as methanol, ethanol or propanol, and acetone. Water is used particularly preferably in the present invention.

Although there are no particular limitations on the concentration of the calcium raw material in the calcium-containing liquid, the solid concentration of the calcium raw material may be normally suitably set to 1% by weight to 30% by weight and preferably to about 1% by weight to 20% by weight.

The alkali is not limited, and examples thereof include sodium hydroxide, potassium hydroxide, ammonia, ammonium salts and aqueous ammonia. At least one type of alkali such as sodium hydroxide or potassium hydroxide can be used particularly preferably. The amount of alkali added is preferably adjusted so that the pH is 8.0 to 13.0 and particularly 11.0 to 12.5. By adding alkali so as to achieve such a pH, the first aqueous slurry containing calcium hydroxide for the first reaction product can be obtained particularly preferably. In particular, calcium ions of a soluble calcium raw material and calcium hydroxide formed in a reaction with alkali (solid calcium compound) are preferably both present in the first aqueous slurry.

Second Step

In the second step, a second aqueous slurry containing a second reaction product is obtained by adding a silicic acid raw material to the above-mentioned first aqueous slurry or an aqueous slurry for which the water content thereof has been adjusted, and allowing to react.

In the second step, although the first slurry obtained in the first step is preferably used as is without adjusting, an aqueous slurry that the water content of the first aqueous slurry has been changed as necessary can also be used.

Calcium ions of a soluble calcium source and solid calcium of calcium hydroxide formed in a reaction with alkali are preferably both present in the first aqueous slurry. As a result of having calcium ions and solid calcium both present in the first aqueous slurry, a porous reaction product can be effectively obtained due to having an effect on reactivity with the silicic acid raw material and pore structure of the reaction product.

Silicic acid similar to that used in the production of known calcium silicate can be used for the silicic acid raw material. Examples thereof include silicon dioxide, sodium silicate, potassium silicate and silica sol. At least one type such as silicon dioxide or sodium silicate can be used particularly preferably.

The amount of silicic acid raw material added is set so that the prescribed calcium silicate is formed. Namely, the molar ratio of $SiO_2/CaO$ is theoretically set to a range of 1.5 to 6.5 and more preferably 1.5 to 5.0.

The silicic acid raw material is mixed with the first reaction product, and allowed to react. As a result, a second reaction product can be obtained that contains a tobermorite-type calcium silicate able to serve as a precursor of the material of the present invention. Normally, the second reaction product can be formed in the form of an aqueous slurry. Although there are no particular limitations thereon, the reaction temperature is preferably suitably set within a range of, for example, 5° C. to 100° C. and particularly 70° C. to 80° C. In addition, the reaction may be carried out in air (under atmospheric pressure). Reaction time can be suitably adjusted corresponding to the reaction temperature. In this manner, the production method of the present invention allows the obtaining of a second reaction product under comparatively mild conditions without relying on a hydrothermal synthesis reaction (using an autoclave apparatus).

Aging Step

In the present invention, the second aqueous slurry or an aqueous slurry for which the water content thereof has been adjusted, is preferably preliminarily supplied to an aging step prior to the third step if necessary. Carrying out this aging step makes it possible to effectively promote formation of a fine pore structure by promoting the reaction of unreacted calcium. From this viewpoint, the aging step is preferably carried out while agitating the second aqueous slurry. Although the aging temperature is not limited, it is typically preferably 50° C. to 70° C. and more preferably 55° C. to 65° C. in particular. Although there are no particular limitations thereon, aging time is normally 0.5 hours to 10 hours and is preferably 1 hour to 1.5 hours. Although there are no particular limitations thereon, the solid concentration of the second aqueous slurry during aging is normally 1% by weight to 30% by weight and more preferably about 3% by weight to 20% by weight.

Third Step

In the third step, a third aqueous slurry containing a tobermorite-type calcium silicate-based material is obtained by adjusting the pH of the second aqueous slurry or an aqueous slurry for which the water content of the second aqueous slurry has been changed.

In the third step, although the second aqueous slurry obtained in the second step is preferably used without adjusting, an aqueous slurry obtained by adjusting the water content of the second aqueous slurry as necessary can also be used.

There are no particular limitations on adjustment of pH provided it is carried out so that the prescribed tobermorite-type calcium silicate-based material is formed from the above-mentioned aqueous slurry. Any acid (such as hydrochloric acid, nitric acid, sulfuric acid or organic acid) or alkali (such as sodium hydroxide) can be used for the pH adjusting agent. In the present invention in particular, pH is preferably adjusted to about 7.0 to 11.0 and particularly preferably adjusted to 8.0 to 10.9. By controlling the pH to be within these ranges, silicon dioxide is precipitated in the aqueous medium, a portion of the calcium in the calcium silicate is dissolved by acid, and mixed crystals of silicon dioxide and tobermorite-type calcium silicate can be prepared. In this manner, a third aqueous slurry can be obtained in which particles of a tobermorite-type calcium silicate-based material are dispersed.

Solid-Liquid Separation Step and Washing Step

In the present invention, although the third aqueous slurry can be used directly as a starting material of various applications, the third aqueous slurry may also be subjected to a solid-liquid separation step, washing step, drying step, grinding step or classification step and the like if necessary.

The solid-liquid separation step can be carried out by dehydrating by ordinary filtration such as pressure filtration, suction filtration, vacuum filtration, natural filtration or centrifugal filtration. At this time, a filter press, centrifuge or other known or commercially available apparatus can be used.

The washing step may be carried out by washing a solid obtained from the above-mentioned solid-liquid separation step. The degree of washing is such that the electrical conductivity of the washing filtrate (25°) is 200 µS/cm to 300 µS/cm and preferably 200 µS/cm to 250 µS/cm.

Although the drying step may consist of air drying or hot air drying, in the case of hot air drying, the temperature range can be normally set to about 60° C. to 120° C. The drying method is preferably carried out by drying under conditions that substantially prevent the generation of shear force. Preferable examples of drying methods used include ventilation drying, instantaneous drying, spray drying, freeze drying, vacuum drying and microwave drying.

In addition, in the grinding step, a method can be used that reduces the likelihood of impurity contamination, and a known grinding method such as shear grinding, disc grinding, roller grinding, cylinder grinding, hammer grinding, jet grinding or high-speed rotary grinding can be used. There are also no limitations on the means used in the classification step, and a known method such as dry sieving in the form of air classification or screen sieving can be used.

In this manner, the material of the present invention represented by the compositional formula $5CaO \cdot 7SiO_2 \cdot nSiO_2 \cdot mH_2O$ (wherein, n and m satisfy the relationships of $0.5 \leq n$ and $0 \leq m$) can be obtained.

Although the resulting material of the present invention can be used as a powder (ungranulated powder) in various types of applications, it can also be further granulated, for example. In the case of granulating, dry granulation or wet granulation may be used. In addition, there are no limitations on the granulation method, for example, any of tumbling granulation, agitation granulation, fluidized bed granulation, compression molding, film deposition treatment, magnetic property treatment, surface modification, sinter molding, vibration molding, pressure swing granulation or vacuum molding can be used. This granulation can be carried out using a known or commercially available granulation apparatus. Among these granulation methods, tumbling granulation or compression granulation is preferable in the present invention because those methods can reduce or prevent a decrease in oil absorption of the material of the present invention.

EXAMPLES

The following provides a more detailed explanation of characteristics of the present invention by indicating examples and comparative examples. However, the scope of the present invention is not limited to the examples. Furthermore, the term "%" described in the examples refers to "% by weight" (wt %).

Example 1

1786 g of water were placed in a 5 L reaction tank followed by heating to a liquid temperature of 72.5° C., adding 179 g of calcium chloride and completely dissolving the calcium chloride. Next, 119 g of 48% sodium hydroxide solution were brought to a volume of 171 mL with water and then dropped into the reaction tank over the course of 30 minutes. Following completion of dropping, 371 mL of liquid of sodium silicate JIS No. 3 were brought to a volume of 1429 mL with water, and then dropped into the reaction tank over the course of 3 hours. Following completion of dropping, the liquid temperature was made to be 60° C. followed by aging for 1 hour. Following completion of aging, the pH of the reaction product was adjusted to 10.4 using 18% hydrochloric acid. After adjusting the pH, the reaction product was washed using a filter press and washing was continued until the electrical conductivity of the filtrate reached 250 µS/cm. After washing, ventilation drying was carried out at 100° C. followed by going through a grinding step to obtain a powder of a tobermorite-type calcium silicate-based material.

Example 2

Example 2 was carried in the same manner as Example 1 up to the aging step, and the pH of the reaction product was adjusted to 10.0 using 18% hydrochloric acid following completion of the aging step. The reaction product was washed using a filter press after adjusting pH, and washing was continued until the electrical conductivity of the filtrate reached 250 µS/cm. Following washing, ventilation drying was carried out at 100° C. followed by going through a grinding step to obtain a powder of a tobermorite-type calcium silicate-based material.

Example 3

Example 3 was carried in the same manner as Example 1 up to the aging step, and the pH of the reaction product was adjusted to 9.0 using 18% hydrochloric acid following completion of the aging step. The reaction product was washed using a filter press after adjusting pH, and washing was continued until the electrical conductivity of the filtrate reached 250 μS/cm. Following washing, ventilation drying was carried out at 100° C. followed by going through a grinding step to obtain a powder of a tobermorite-type calcium silicate-based material.

Example 4

Example 4 was carried in the same manner as Example 1 up to the aging step, and the pH of the reaction product was adjusted to 8.0 using 18% hydrochloric acid following completion of the aging step. The reaction product was washed using a filter press after adjusting pH, and washing was continued until the electrical conductivity of the filtrate was 250 μS/cm. Following washing, ventilation drying was carried out at 100° C. followed by going through a grinding step to obtain a powder of a tobermorite-type calcium silicate-based material.

Example 5

1786 g of water were placed in a 5 L reaction tank followed by heating to a liquid temperature of 72.5° C., adding 179 g of calcium chloride and completely dissolving the calcium chloride. Then, 203 g of 48% sodium hydroxide solution were brought to a volume of 171 mL with water and then dropped into the reaction tank over the course of 30 minutes. Following completion of dropping, 371 mL of liquid of sodium silicate JIS no. 3 were brought to a volume of 1429 mL with water and then dropped into the reaction tank over the course of 3 hours. Following completion of dropping, the liquid temperature was made to be 60° C. followed by aging for 1 hour. Following completion of aging, the pH of the reaction product was adjusted to 10.9 using 18% hydrochloric acid. After adjusting the pH, the reaction product was washed using a filter press and washing was continued until the electrical conductivity of the filtrate reached 250 μS/cm. After washing, ventilation drying was carried out at 100° C. followed by going through a grinding step to obtain a powder of a tobermorite-type calcium silicate-based material.

Example 6

Example 6 was carried in the same manner as Example 5 up to the aging step, and the pH of the reaction product was adjusted to 10.0 using 18% hydrochloric acid following completion of the aging step. The reaction product was washed using a filter press after adjusting pH, and washing was continued until the electrical conductivity of the filtrate was 250 μS/cm. Following washing, ventilation drying was carried out at 100° C. followed by going through a grinding step to obtain a powder of a tobermorite-type calcium silicate-based material.

Example 7

Example 7 was carried in the same manner as Example 5 up to the aging step, and the pH of the reaction product was adjusted to 9.0 using 18% hydrochloric acid following completion of the aging step. The reaction product was washed using a filter press after adjusting pH, and washing was continued until the electrical conductivity of the filtrate was 250 μS/cm. Following washing, ventilation drying was carried out at 100° C. followed by going through a grinding step to obtain a powder of a tobermorite-type calcium silicate-based material.

Example 8

Example 8 was carried in the same manner as Example 5 up to the aging step, and the pH of the reaction product was adjusted to 8.0 using 18% hydrochloric acid following completion of the aging step. The reaction product was washed using a filter press after adjusting pH, and washing was continued until the electrical conductivity of the filtrate was 250 μS/cm. Following washing, ventilation drying was carried out at 100° C. followed by going through a grinding step to obtain a powder of a tobermorite-type calcium silicate-based material.

Comparative Example 1

"NF Calcium Silicate" (Lot No. H30306) manufactured by Tomita Pharmaceutical Co., Ltd. was used as a commercially available tobermorite-type calcium silicate-based material containing silicon dioxide.

Comparative Example 2

"Tobermorite Powder TK" (Lot No. TK11030204101) manufactured by Japan Insulation Co., Ltd. was used as commercially available tobermorite-type calcium silicate.

Comparative Example 3

20.2 g of "Tobermorite Powder TK" (Lot No. TK11030204101) manufactured by Japan Insulation Co., Ltd. and 5.3 g of "Aerosil 200" (Lot No. 614020181) manufactured by Evonik Degussa GmbH were weighed in a plastic bag and the plastic bag was sealed in an expanded state followed by mixing well for 5 minutes to obtain a mixed powder consisting of a tobermorite-type calcium silicate powder and silicon dioxide powder.

Test Example 1

Figure 2:
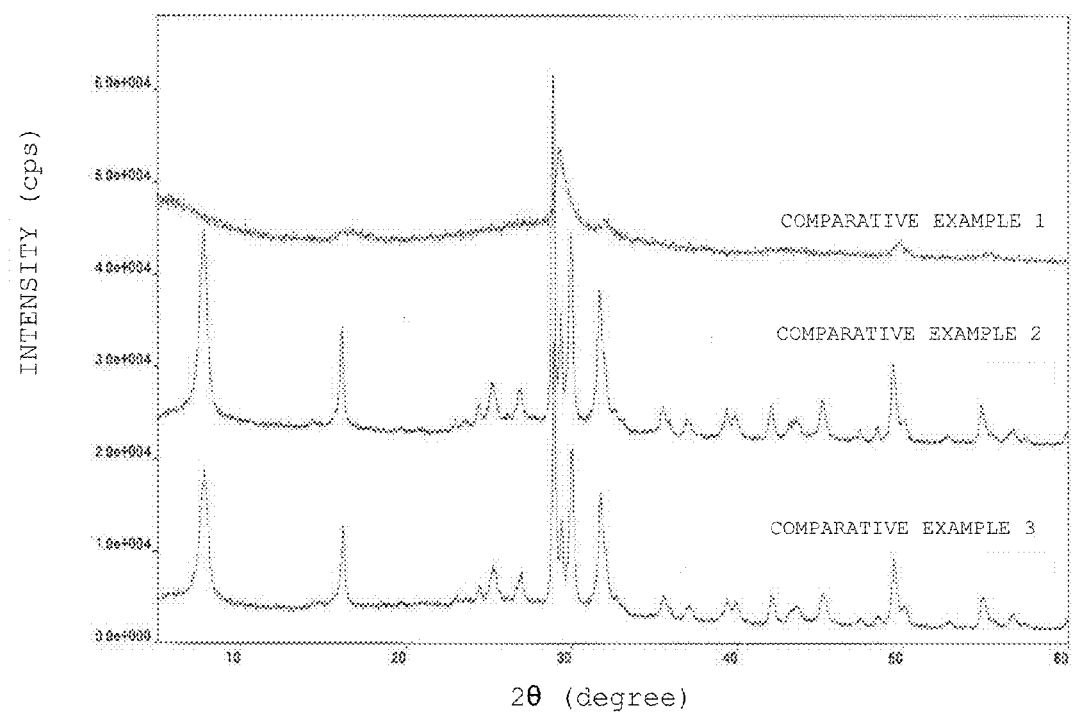
FIG. 2 is a graph showing the results of analyzing each of the samples of Comparative Examples 1 to 3 by powder X-ray diffraction analysis.
Figure 3:
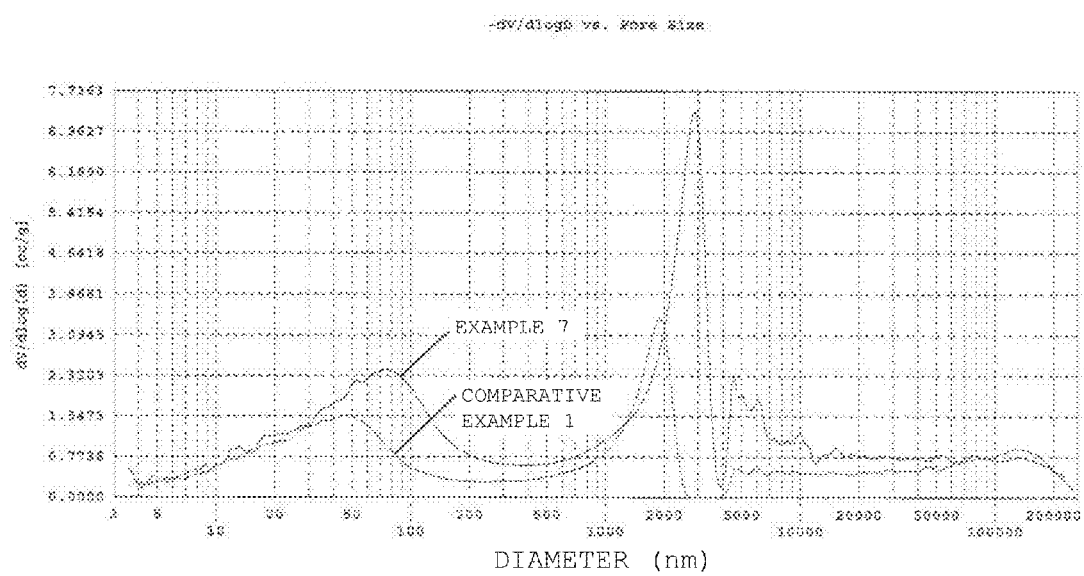
FIG. 3 is a graph showing the results of measuring the pore distributions of Example 7 and Comparative Example 1 by mercury penetration method.
Figure 4:
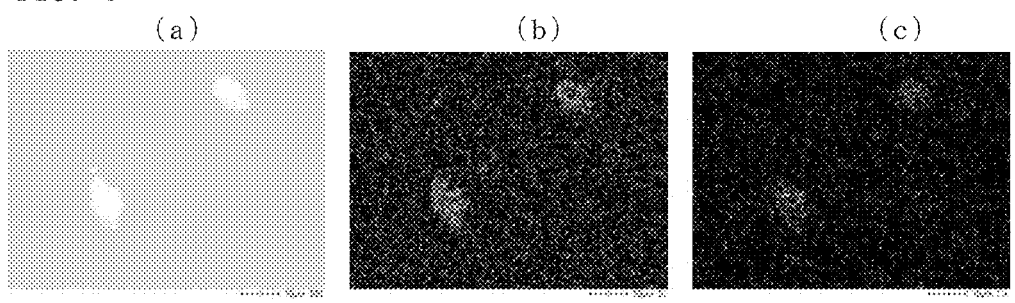
FIG. 4($a$) is an image showing the results of observing the sample of Example 7 with a scanning electron microscope (SEM), FIG. 4($b$) is an image showing the results of measuring the element distribution of silicon in the sample of Example 7 using energy dispersive X-ray spectroscopy (EDS), and FIG. 4($c$) is an image showing the results of measuring the element distribution of calcium in the sample of Example 7 using energy dispersive X-ray spectroscopy (EDS)
Figure 5:
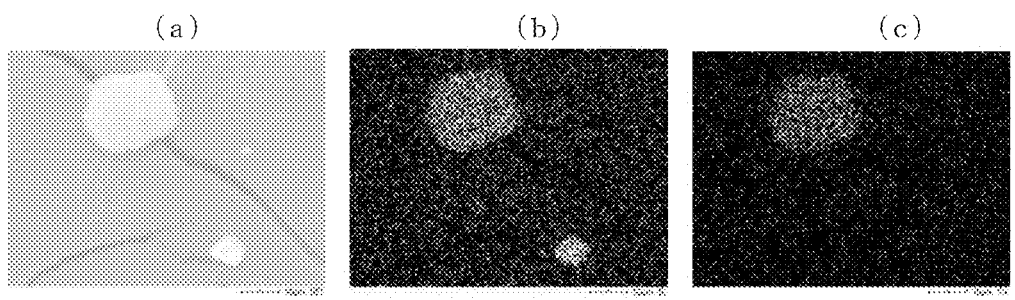
FIG. 5($a$) is an image showing the results of observing the sample of Comparative Example 3 with an SEM, FIG. 5($b$) is an image showing the results of measuring the element distribution of silicon in the sample of Comparative Example 3 using energy dispersive X-ray spectroscopy (EDS), and FIG. 5($c$) is an image showing the results of measuring the element distribution of calcium in the sample of Comparative Example 3 using energy dispersive X-ray spectroscopy (EDS)

Each of the samples obtained in Examples 1 to 8 and Comparative Examples 1 to 3 were measured for oil absorption, cumulative pore volume, BET specific surface area, average particle diameter, bulk specific volume, silicon dioxide content, calcium oxide content, $SiO_2/CaO$ molar ratio, crystal structure, integrated intensity, integrated intensity ratio and element distribution. The results are shown in Table 1. The results of powder X-ray diffraction analysis are shown in FIGS. 1 and 2, measurement results obtained by mercury penetration method are shown in FIG. 3, and the results of measuring element distribution are shown in FIGS. 4 and 5 as related to the above-mentioned measurements. Furthermore, each measurement was carried out in accordance with the methods described below.

(1) Oil Absorption 1.0 g of sample was weighed out and placed on a black plastic plate. 4 to 5 drops at a time of boiled linseed oil contained in a pipette were dropped onto the plate from above followed by adequately kneading with the powder each time using a spatula. The boiled linseed oil was kneaded with the powder at each one drop at a time once the entire mixture became a clump in the form of a hard putty. Dropping was terminated immediately prior to the mixture suddenly becoming soft with the final drop, and the amount of boiled linseed oil dropped onto the sample was recorded followed by calculating oil absorption according to the equation indicated below.

Oil absorption (mL/g)=Amount of boiled linseed oil dropped (mL)/sample weight (g)

(2) Cumulative Pore Volume

Cumulative pore volume was measured under the following conditions with the "Poremaster 60GT" mercury porosimeter manufactured by Quantachrome Instruments. 0.05 g of sample were sealed in a measuring cell and cumulative pore volume was calculated from the measured pressure using a mercury contact angle of 140° and mercury surface tension of 480 dyn/cm. Furthermore, analysis ranges over a pore size of 3.6 nm to 200 nm, 200 nm to 5000 nm and 3.6 nm to 5000 nm were used for the analysis range.

(3) BET Specific Surface Area

BET specific surface area was measured under the following conditions with a high-speed specific surface area pore distribution measuring apparatus (NOVA-4000e, Quantachrome Instruments).

Pretreatment conditions: 0.02 g of sample were accurately weighed out and sealed in an adsorption tube followed by degassing for 1 hour at 105° C.

Measurement and analysis: The adsorption isotherm of nitrogen gas was determined at the gas temperature of liquid nitrogen followed by calculation of BET specific surface area according to the multipoint BET method at relative pressures of 0.1, 0.2 and 0.3.

(4) Average Particle Diameter

A sample was dispersed in water after subjecting to ultrasonic agitation for 3 minutes (ultrasonic output: 40 W) followed by measuring average particle diameter in an aqueous medium by laser diffraction. The "Microtrac MT3300EX II" manufactured by MicrotracBEL Corp. was used for the measuring apparatus.

(5) Bulk Specific Volume 3.0 g of sample were weighed out and placed in a 50 mL graduated cylinder followed by tapping at a height of 4 cm and speed of 100 times/250 seconds, measuring powder volume and calculating bulk specific volume according to the equation indicated below.

Bulk specific volume (mL/g)=Powder volume (mL)/powder weight (g)

(6) Quantification of Silicon Dioxide Content

Approximately 0.4 g of sample were accurately weighed out after drying followed by placing in a beaker, adding 20 mL of water and 10 mL of perchloric acid, and heating until white smoke was produced. The beaker was then covered with a watch glass and further heated for 15 minutes. After cooling, 30 mL of water were added, the mixture was filtered with filter paper for quantitative analysis (JIS No. 5C), and the residue was washed with 1 L of hot water. The filtrate and washing were mixed and designated as Liquid A. The residue remaining on the filter paper was placed in a platinum crucible along with the filter paper followed by heating and drying, ashing, and igniting at 900° C. to 1000° C. After allowing to cool in a desiccator, the weight W (g) thereof was measured. 5 drops of sulfuric acid and 15 mL of hydrofluoric acid were added to the residue followed by carefully heating until a dried solid was obtained from the residue, heating at about 1000° C. until the weight was constant, allowing to cool in a desiccator and measuring the weight w (g) thereof. The silicon dioxide content was determined according to the equation indicated below.

Silicon dioxide content (%)=(W(g)−w(g))/sample weight (g)×100(%)

(7) Quantification of Calcium Oxide Content

Liquid A obtained during quantification of silicon dioxide content was neutralized with a 1 mol/L aqueous sodium hydroxide solution, and 10 mL of a 0.05 mol/L EDTA solution were added to the neutralized solution using a 50 mL biuret while stirring the neutralized solution. 15 mL of a 1 mol/L aqueous sodium hydroxide solution and 300 mg of hydroxynaphthol blue were added followed by titrating with the 0.05 mol/L EDTA solution. The endpoint was defined as the point at which the reddish-purple color of the liquid completely disappeared and became blue. The titrated volume V (mL) at that time was recorded and calcium oxide content was determined according to the equation indicated below.

1 ml of 0.05 mol/L EDTA solution=2.804 mg CaO

Calcium oxide content (%)=2.804 (mg/mL)×V(mL)×F/sample weight (mg)×100(%)

F: 0.05 mol/L EDTA factor of solution (8) $SiO_2$/CaO Molar Ratio $SiO_2$/CaO molar ratio was calculated according to the following equation using the values obtained from the quantification procedures described above.

$SiO_2$/CaO molar ratio=(silicon dioxide content (%)/silicon dioxide molecular weight)/(calcium oxide content (%)/calcium oxide molecular weight)

(9) Powder X-Ray Diffraction Analysis

Measurements were carried out over a range of 2θ=5° to 60° with the "SmartLab (3 kw)" X-ray analyzer (Rigaku Corp.). Measurement conditions consisted of using Cu for the target, tube voltage of 40 kV, tube current of 20 mA, scanning range of 5° to 60°, scanning speed of 10.000°/min, scanning step of 0.02°, using a continuous scan mode, using the kβ filter method, divergence slit of 1°, scattering slit of 1° and receiving slit of 0.15 mm.

(10) Integrated Intensity

The measurement results obtained in the powder X-ray diffraction analysis were analyzed using Rigaku Data Analysis Software PDXL Version 2.0.3.0. First, two points at which integrated intensity was low as determined according to the measurement results were connected followed by background compilation. Next, the peak locations represented by 2θ/θ at 5.47°, 16.61°, 25.00°, 29.24°, 32.00°, 42.40°, 49.85° and 55.29° were fixed. Continuing, optimization was selected, selection of the parameter "background refinement" was cancelled and custom was selected to fix the locations of all peaks. The asymmetry factor was set to 1 for 29.24° and 32.00°. The split pseudo-Voigt function was selected for peak shape, and measurements were carried out four times. The integrated intensity of each peak was obtained from those measurements.

(11) Integrated Intensity Ratio

Integrated intensity ratio was calculated according to the equation indicated below.

Integrated intensity ratio=(integrated intensity at 32.00°)/(integrated intensity at 25.00°)

(12) Measurement of Element Distribution

A sample was fixed to a piece of carbon tape and subjected to gold deposition to obtain a measurement sample. Measurement was carried out by capturing secondary electron images (SEM images) at an accelerating voltage of 15 kV using a scanning electron microscope ("JSM-5500LV", JEOL Ltd.), followed by measuring element distribution from the intensities of characteristic X-rays derived from silicon and calcium at an accelerating voltage of 15 kV using an energy dispersive x-ray spectrometer (EDS, "JED-2200", JEOL Ltd.).

advantages of the present invention cannot be obtained simply by mixing so that the molar ratio of $SiO_2/CaO$ of a powder composition is in the vicinity of 2.0 in this manner.

TABLE 1

|  | Examples | | | | | | | | Comparative Examples | | |
| --- | --- | --- | --- | --- | --- | --- | --- | --- | --- | --- | --- |
|  | 1 | 2 | 3 | 4 | 5 | 6 | 7 | 8 | 1 | 2 | 3 |
| pH after dropping HCl | 10.4 | 10.0 | 9.0 | 8.0 | 10.9 | 10.0 | 9.0 | 8.0 | — | — | — |
| Oil absorption (mL/g) | 3.0 | 3.1 | 2.9 | 2.7 | 2.9 | 3.3 | 3.9 | 3.7 | 2.1 | 2.5 | 1.7 |
| Cumulative pore volume 1* (cc/g) | 1.63 | 1.83 | 1.66 | 1.73 | 1.00 | 1.63 | 2.18 | 1.82 | 1.39 | 0.56 | 0.84 |
| Cumulative pore volume 2* (cc/g) | 2.01 | 1.62 | 1.65 | 1.88 | 2.33 | 2.07 | 2.47 | 2.45 | 1.10 | 3.87 | 3.69 |
| Cumulative pore volume 3* (cc/g) | 3.64 | 3.45 | 3.31 | 3.63 | 3.33 | 3.70 | 4.65 | 4.27 | 2.50 | 4.46 | 4.56 |
| BET specific surface area ($m^2/g$) | 231.9 | 150.5 | 163.0 | 165.6 | 200.3 | 139.8 | 153.5 | 167.3 | 172.2 | 58.0 | 192.7 |
| Average particle diameter (μm) | 20.0 | 20.8 | 21.9 | 22.8 | 10.6 | 9.4 | 10.8 | 11.6 | 13.4 | 22.7 | 21.6 |
| Bulk specific volume (mL/g) | 6.8 | 7.0 | 7.0 | 7.3 | 5.3 | 6.7 | 8.7 | 8.3 | 4.7 | 9.5 | 10.1 |
| $SiO_2$ (%) | 53.8 | 52.9 | 54.0 | 61.0 | 49.3 | 48.6 | 52.5 | 57.0 | 55.9 | 46.7 | 57.0 |
| CaO (%) | 26.4 | 25.7 | 24.5 | 19.6 | 31.0 | 29.6 | 26.0 | 22.9 | 25.8 | 34.7 | 28.0 |
| $SiO_2/CaO$ | 1.9 | 2.0 | 2.2 | 2.9 | 1.5 | 1.5 | 1.9 | 2.3 | 2.2 | 1.3 | 1.9 |
| 25.00° integrated intensity (cps) | 21822 | 23579 | 22557 | 27418 | 15629 | 16152 | 21575 | 23627 | 16127 | 17988 | 20917 |
| 32.00° integrated intensity (cps) | 1485 | 1382 | 1185 | 716 | 2357 | 2175 | 1609 | 1036 | 2359 | 3970 | 4524 |
| Integrated intensity ratio | 0.07 | 0.06 | 0.05 | 0.03 | 0.15 | 0.13 | 0.07 | 0.04 | 0.14 | 0.22 | 0.22 |

*Cumulative pore volume 1, 2 and 3 were measured by mercury penetration method over a pore size range of 3.6 nm to 200 nm for cumulative pore volume 1, 200 nm to 5000 nm for cumulative pore volume 2, and 3.6 nm to 5000 nm for cumulative pore volume 3.

As is clear from the results shown in Table 1, Examples 1 to 8 can be understood to have reached a cumulative pore volume having a pore size of 3.6 nm to 200 nm of 0.9 cc/g or more and a cumulative pore volume having a pore size of 3.6 nm to 5000 nm of 2.6 cc/g or more. In addition, the molar ratios of $SiO_2/CaO$ were from 1.5 to 2.9, and effects can be understood to be maximized particularly in the vicinity of an $SiO_2/CaO$ molar ratio of 2.0.

As can be understood from FIGS. 1 and 2, although peaks corresponding to tobermorite-type calcium silicate were detected in Examples 1 to 8 and Comparative Example 1, peaks derived from tobermorite-type calcium silicate in the vicinity of 25° were apparently no longer detected due to the presence of amorphous substances derived from the silica component, and were determined to be different from the XRD pattern of tobermorite-type calcium silicate crystals alone.

As is clear from FIG. 3, a comparison of Example 7 and Comparative Example 1 revealed that pores having a pore size of 3.6 nm to 200 nm and particle gaps measuring 1000 nm to 5000 nm are more prominent in Example 7. As a result, oil can be retained by particle aggregated space and the pore in primary particles, thereby resulting in Example 7 demonstrating higher oil absorption than Comparative Example 1.

As is clear from FIGS. 4 and 5, since individual particles contained a silicon component and a calcium component and expressed a pore structure derived from the silica component in Example 7, pores developed and resulted in a higher level of oil absorption. Since silicon dioxide powder and calcium silicate powder were merely dry-mixed in Comparative Example 3, a silica component and calcium component were not contained in a single particle. This demonstrates that the Example 9

The tobermorite-type calcium silicate-based material obtained in Example 3 was subjected to dry granulation with the "Roller Compactor TF-MINI" manufactured by Freund Corp. under the conditions of DPS for the roller shape, roller pressure of 15 kN, roller speed of 10 rpm, screw speed of 10 rpm, and oscillator screen openings of 1 mm. Subsequently, the particles were classified with a sieve to obtain granules having a particle diameter of 180 μm to 500 μm. On the other hand, 45 g of sodium ascorbate, 8 g of ferrous sulfate heptahydrate and 10 g of sodium carbonate were dissolved in 55 g of water to prepare a main agent solution. Then, 60 g of the above-mentioned main agent solution were added to 20 g of the resulting granules and impregnated therein while mixing to obtain a deoxidizing agent.

Example 10

Dry granulation was carried out using a mixture obtained by mixing 354 g of the tobermorite-type calcium silicate-based material obtained in Example 3, 270 g of sodium ascorbate, 48 g of the ferrous sulfate heptahydrate and 60 g of sodium carbonate under the same conditions as Example 9 with the exception changing the screw speed to 6 rpm. 11 g of water were added to 24.4 g of the resulting granules and impregnated therein while mixing to obtain a deoxidizing agent.

Test Example 2

Deoxidizing capacity and angle of repose were measured for the deoxidizing agents obtained in Examples 9 and 10.

Figure 6:
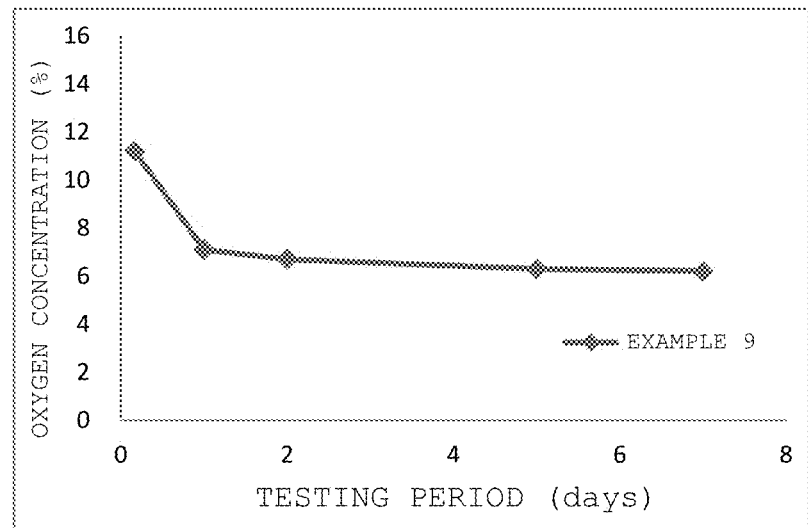
FIG. 6 is a graph showing the results of a deoxygenation test of a deoxidizing agent obtained in Example 9.
Figure 7:
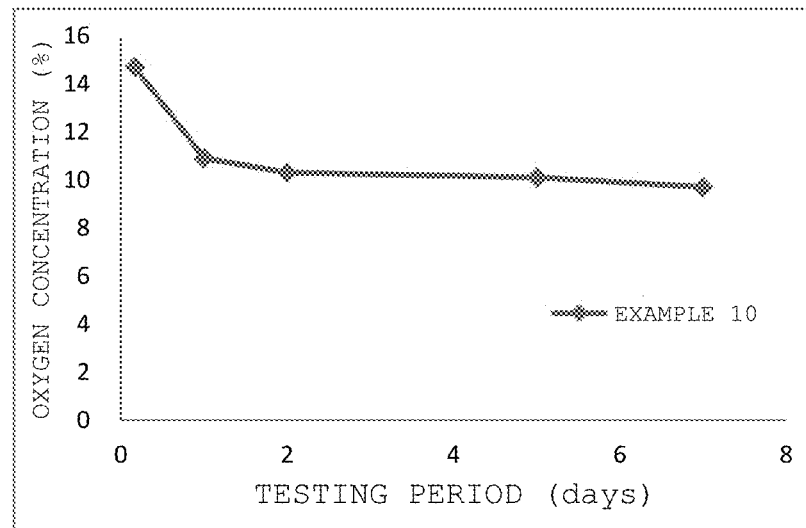
FIG. 7 is a graph showing the results of a deoxygenation test of a deoxidizing agent obtained in Example 10.

The results are shown in Table 2 and FIGS. 6 and 7. Each measurement was carried out based on the methods described below.

(13) Deoxidizing Capacity 4 g of deoxidizing agent were filled into a bag made of a nonwoven fabric of polyethylene and polypropylene and sealed in an "Aluminum Bag" manufactured by GL Sciences Inc. Next, 2 L of air (oxygen concentration: 20.9%) in a constant-temperature, constant-humidity chamber set to 25° C. and 60% RH were filled into the aluminum bag in the chamber and allowed to stand undisturbed. Subsequently, oxygen concentrations at 4 hours, 1 day, 2 days, 5 days and 7 days later, based on an air filling time of 0 hours, were measured with the "OX-01 Oxygen Gas Monitor" manufactured by Riken Keiki Co., Ltd.

(14) Angle of Repose

Angle of repose was measured with the "Powder Tester PT-X" manufactured by Hosokawa Micron Corp. Measurements were carried out at a vibration amplitude of 0.5 mm and vibration time of 170 seconds using a sieve having an opening size of 710 μm.

TABLE 2

| Example | Angle of repose (°) | Oxygen concentration (%) | | | | |
|---|---|---|---|---|---|---|
| | | 4 hours | 1 day | 2 days | 5 days | 7 days |
| 9 | 43.0 | 11.2 | 7.1 | 6.7 | 6.3 | 6.2 |
| 10 | 52.1 | 14.7 | 10.9 | 10.3 | 10.1 | 9.7 |

As is clear from the results of Table 2, the tobermorite-type calcium silicate-based materials of Examples 9 and 10 can be understood to be effective as carriers of a deoxidizing agent.

Test Example 3

The melanin adsorbing capacity of each of the samples obtained in Example 3 and Comparative Example 2 was measured. The results are shown in Table 3. Each measurement was carried out based on the method described below.

(Melanin Adsorbing Capacity)

20 ml of a melanin solution were added to 0.1 g of sample, shaken for 1 hour at room temperature with a shaker and centrifuged at room temperature for 15 minutes at a rotating speed of 3000 rpm using the "RLX-135 Centrifuge" manufactured by Tomy Seiko Co., Ltd., followed by collecting the supernatant liquid and using as a test liquid. The test liquid was measured for optical absorbance at a wavelength of 470 nm using the "V-660 Spectrophotometer" manufactured by Jasco Corp., and melanin adsorption rate was measured according to the equation indicated below.

Melanin adsorption rate (%)=(1−optical absorbance of test liquid/optical absorbance of melanin solution)×100

Furthermore, the above-mentioned melanin solution was prepared by adding 200 ml of a 0.01 mol/L sodium hydroxide aqueous solution to 0.040 g of "Dry Melanin" manufactured by Fuji Molecular Planning Co., Ltd. followed by dissolving by stirring for 2 hours in a water bath at 60° C. and adding 0.07 mol/L phosphate buffer (pH 5.5). In addition, the solution was centrifuged at room temperature for 15 minutes at a rotating speed of 3000 rpm using the "RLX-135 Centrifuge" manufactured by Tomy Seiko Co., Ltd. followed by collecting the supernatant liquid. 0.07 mol/L phosphate buffer (pH 5.5) was added to the supernatant liquid so that optical absorbance at a wavelength of 470 nm as measured using the "V-660 Spectrophotometer" manufactured by Jasco Corp. indicated a value of 0.90 to 1.00 to obtain the melanin solution (aqueous solution).

TABLE 3

| Test Example 3 | Melanin adsorption rate (%) |
|---|---|
| Example 3 | 76.2 |
| Comparative Example 2 | 64.4 |

As is clear from the results of Table 3, the tobermorite-type calcium silicate-based material of Example 3 demonstrated a melanin adsorption rate of 70% or more, and particularly 75% or more, and can be understood to be able to adsorb or support a large amount of melanin. Melanin adsorbents incorporating keratolytic agents are contained in cosmetics for the purpose of promoting elimination of melanin formed in skin, and the powdered tobermorite-type calcium silicate-based material of the present invention can be expected to be applied to a cosmetic article having performance that adsorbs and removes melanin. In addition, calcium silicate-based materials loaded with melanin are contained in cosmetics for the purpose of blocking ultraviolet light, and the powdered tobermorite-type calcium silicate-based material of the present invention can also be expected to be applied to cosmetics having performance that protects skin against ultraviolet light.

The invention claimed is:

1. A powdered tobermorite-type calcium silicate-based material, wherein
   (1) a molar ratio of $SiO_2/CaO$ in the material is 1.5 or more, and
   (2) a cumulative pore volume having a pore size of 3.6 nm to 200 nm in the material is 0.9 cc/g or more, and a cumulative pore volume having a pore size of 3.6 nm to 5000 nm is 2.6 cc/g or more.

2. The powdered tobermorite-type calcium silicate-based material according to claim 1, wherein an integrated intensity ratio during powder X-ray diffraction analysis [(integrated intensity when peak location represented by $2\theta/\theta=32.00°$)/(integrated intensity when peak location represented by $2\theta/\theta=25.00°$)] is 0.01 to 0.20.

3. The powdered tobermorite-type calcium silicate-based material according to claim 1, wherein a BET specific surface area is 100 $m^2/g$ to 500 $m^2/g$.

4. The powdered tobermorite-type calcium silicate-based material according to claim 1, wherein an average particle diameter is 1 μm to 100 μm.

5. A method for producing the powdered tobermorite-type calcium silicate-based material according to claim 1, the method comprising:
   (1) a first step of obtaining a first aqueous slurry containing a first reaction product by adding an alkali to a calcium-containing liquid which is prepared by dispersing or dissolving a calcium raw material in an aqueous medium, and allowing to react;
   (2) a second step of obtaining a second aqueous slurry containing a second reaction product by adding a silicic acid raw material to the first aqueous slurry, and allowing to react, and aging the second reaction product for a fixed period of time at 70° C. or lower, and wherein the amount of silicic acid raw material added in such that the molar ratio of $SiO_2/CaO$ is theoretically set to a range of 1.5 to 6.5; and (3) a third step of obtaining a third aqueous slurry containing a tobermorite-type calcium silicate-based material by adjusting pH of the second aqueous slurry.

6. A deoxidizing agent comprising the powdered tobermorite-type calcium silicate-based material according to claim 1 and an easily oxidizable component supported on the material.

7. A cosmetic containing the powdered tobermorite-type calcium silicate-based material according to claim 1.

8. The cosmetic according to claim 7 comprising melanin supported on the powdered tobermorite-type calcium silicate-based material.

\* \* \* \* \*